United States Patent [19]

McCullough

[11] Patent Number: 5,447,918
[45] Date of Patent: Sep. 5, 1995

[54] GASTROINTESTINAL ANTI-IRRITANT COMPOSITION COMPRISING SUCRALFATE AND METHODS OF USE

[76] Inventor: Ricky W. McCullough, 165 Crary St., Providence, R.I. 02903

[21] Appl. No.: 205,383

[22] Filed: Mar. 4, 1994

Related U.S. Application Data

[60] Continuation-in-part of Ser. No. 77,715, Jun. 17, 1993, abandoned, which is a division of Ser. No. 919,740, Jul. 27, 1992, abandoned.

[51] Int. Cl.$^6$ .................... A01N 43/04; A61K 31/715
[52] U.S. Cl. .......................... 514/53; 514/54; 514/63; 514/277; 514/365; 514/396; 514/471; 514/574; 514/561; 424/686; 424/687; 424/688
[58] Field of Search ............... 514/53, 54, 61, 390, 514/63, 396; 424/686

[56] References Cited

U.S. PATENT DOCUMENTS

| | | | |
|---|---|---|---|
| 3,432,489 | 3/1969 | Nitta et al. | 260/234 |
| 3,838,150 | 9/1974 | Sugiura et al. | 536/121 |
| 4,975,281 | 12/1990 | Harwood et al. | 514/53 |
| 5,013,557 | 5/1991 | Tai | 424/493 |
| 5,084,446 | 1/1992 | Baldoni et al. | 514/53 |
| 5,234,908 | 8/1993 | Szabo et al. | 514/12 |
| 5,244,670 | 9/1993 | Upson et al. | 424/439 |
| 5,260,304 | 11/1993 | Gergely et al. | 514/58 |

OTHER PUBLICATIONS

Evreux, The Am. J. of Med., 83 (suppl 3B):48–50, (Sep. 28, 1987).
1992 Physician'Desk Reference-pp. 1326–1327.
1986, 1990, 1991, 1992, 1999 AMA Drug Evaluations-p. 1:20–2.
1984 Compendium of Drug Therapy by Biomedical Information Corp p. 32:1.

*Primary Examiner*—Douglas W. Robinson
*Assistant Examiner*—Maria Luisa Osoteo

[57] ABSTRACT

A composition comprising sucralfate and one or more anti-acid epigastralgic relieving agents in a weight ratio of between 0.5:1.0 to 1.3 sucralfate to anti-acid epigastralgic relieving agent and a method of using the composition for relieving symptoms of gastrointestinal mucosal irritation in mammals. The composition may be either in liquid or solid dose form having a combined composition weight percentage of 10–30% per 5 milliliter volume of liquid or 40–85% per solid unit dose form.

12 Claims, 4 Drawing Sheets

FIGURE 1  Plot 1
Rate of Rise to Therapeutic Onset
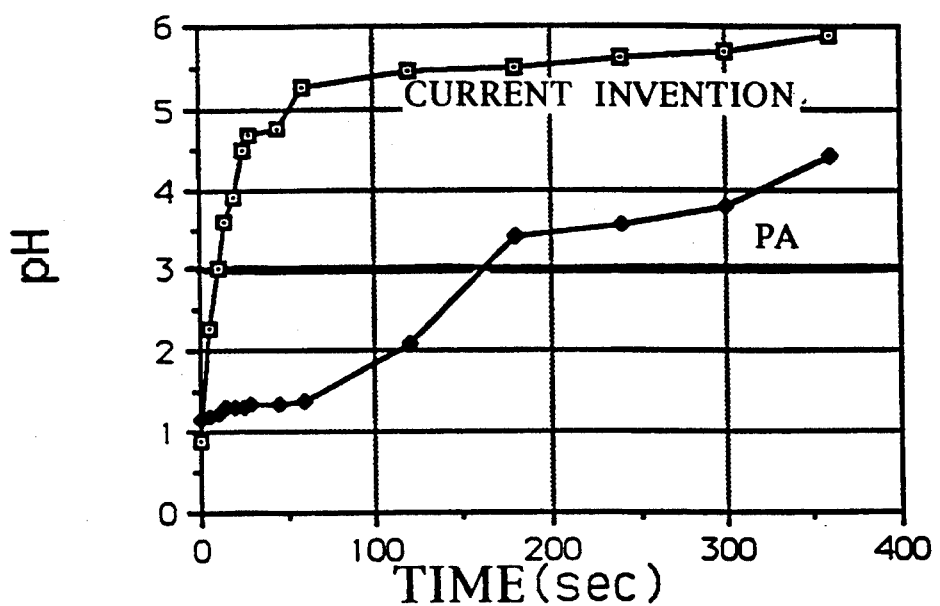

FIGURE 1   Plot 2
Modified Beekman Neutrializtion Test
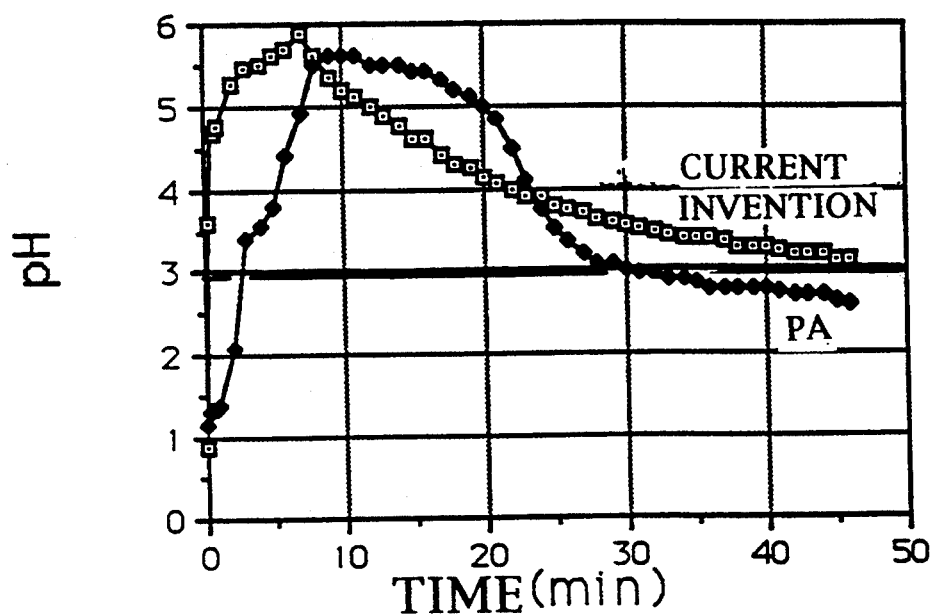

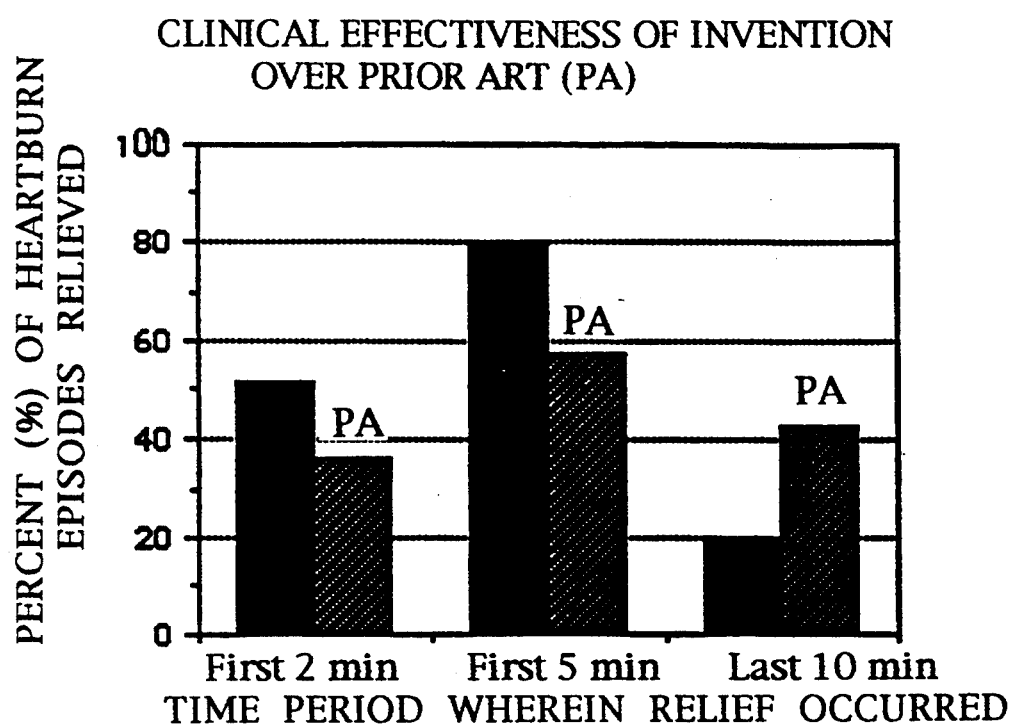
FIGURE 2 Bar Graph 1

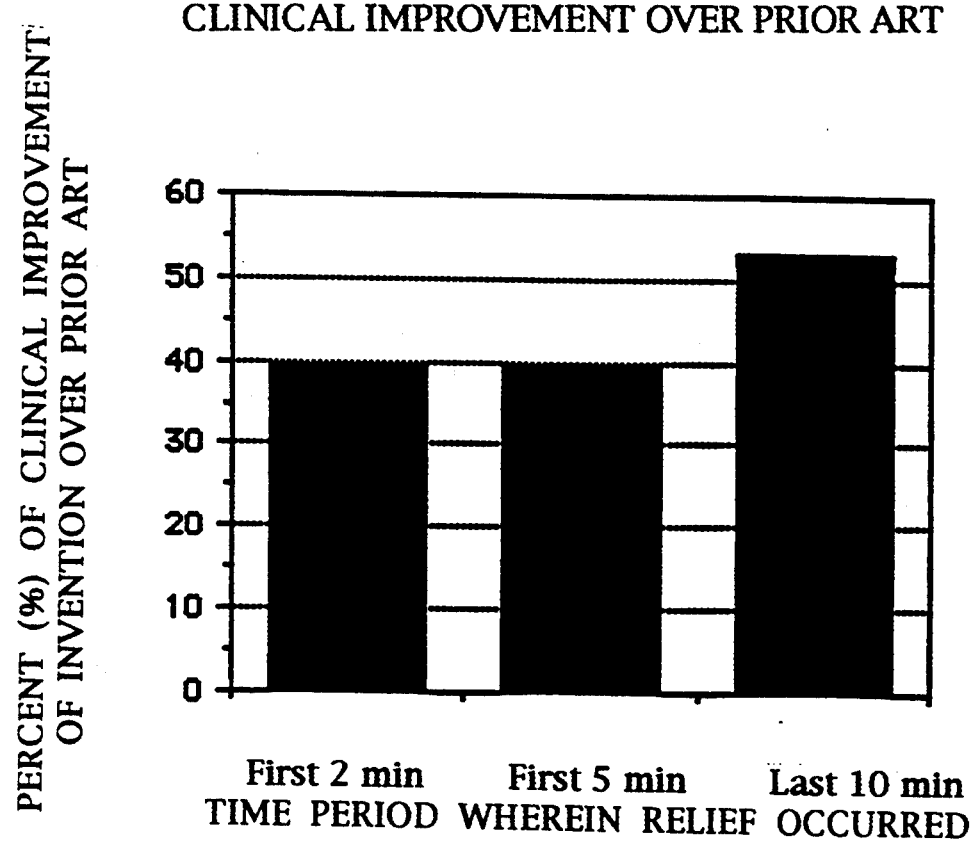
FIGURE 2   Bar Graph 2

GASTROINTESTINAL ANTI-IRRITANT COMPOSITION COMPRISING SUCRALFATE AND METHODS OF USE

CROSS REFERENCE TO RELATED DISCLOSURE

This application is a continuation-in-part of application Ser. No. 08/077,715, filed Jun. 17, 1993, now abandoned, which is a division of application Ser. No. 07/919,740, filed on Jul. 27, 1992, now abandoned.

BACKGROUND

Field of Invention

The present invention relates to novel pharmaceutical compositions of matter comprising functionalized carbohydrates and one or more epigastralgic relieving agents or functionalized carbohydrates created to minimize gastrointestinal (GI) irritation. Whether the GI irritation is due to intrinsic disease states or brought on by the intraluminal introduction of agents of potentially irritating effects, the compositions of this invention effectively minimize mucosal irritation. The combination of functionalized carbohydrates, particularly poly[-phosphory/sulfon]-ated carbohydrates, with epigastralgla-relieving agents impart to said agents the ability to bind bile acids/salts, miligate the local effects of gastric acidity and diminish pepsinogenic activity in gastric secretions, said ability not normally inherent to the agents prior to their combination with the poly[phosphoryl/sulfon]-ated carbohydrate. The novelty of this invention is both the said compositions as well as the method of their use; they are used to prevent and/or treat events of GI mucosal irritation.

BACKGROUND

Description of Prior Art

Gastrointestinal irritation is a problem brought on either by the noxious effects of naturally occurring digestive agents or by the introduction of external agents particularly those taken for analgesia. In either case the irritation, more often than not, is localized to the mucosal lining exhibiting visible evidence of cell loss [Ref 13], microscopic bleeding [Ref 12] and may progress to complete excavative erosions commonly known as ulcer disease. These irritations can occur in the upper or lower alimentary tract and usually have associated somatic symptoms of discomfort. When it involves the epigastric area the discomfort is called heartburn, acid indigestion or sour stomach and is usually accompanied by sensations of bloating. These symptoms of discomfort is often a sensation of gaseous fullness with a gnawing or burning quality occassionally associated with belching. Frank abdominal pain may also occur. Typically these symptoms of gastrointestinal irritation is caused by the presence of internal irritants resident in that portion of the alimentary tract. These irritants include gastric acid, bile acid and salts, and pepsins. Disorders including esophagitis, gastritis, duodenitis and occasionally colitis may result from persistent presence of this group of irritants. See The Merck Manual, 14th Edition, 1982, pg 713, 720 & 724.

The same symptoms and physical effects can occur with internally introduced external agents such as anti-inflammatory analgesics. Non-steroidal anti-inflammatory drugs (NSAID) are widely administered orally [some forms, rectally] in the treatment of mild to severe pain. Commonly used members of this group include aspirin, diflunisal [Dolobid], ibuprofen [Motrin], naproxen [Naprosyn], fenoprofen [Nalfon], piroxicam [Feldene] and mefenamic acid [Ponstel]. See Physicians' Desk Reference 44th Edition (1990) [Ref 8] and The Merck Manual 10th Edition, Merck & Co. Rahway N.J. (1983) for information on specific nonsteroidal anti-inflammatory agents. Each group of irritant agents, the naturally occuring ones and the anti-inflammatory analgesics, can and do cause gastrointestinal irritation. However, regardless of etiology of symptoms and physical signs of the gastrointestinal irritation, the present invention has a novel therapeutic anti-irritant effect quite distinct from the usually methods of treatment or prevention of said symptoms and physical signs of the gastrointestinal irritation. Customarily, the treatment or prevention centers on diminishing gastric acidity which is generally accomplished by either neutralization, decreasing acid production or increasing gastric emptying to limit GI exposure to irritants. There are compounds to address each task. However, none of these pharmaceutcal modalities bind bile acids/salts, inhibit pepsin activity significantly, or deny the transflux of acid through the mucosal lining. Sucralfate, a functionalized polysulfonated carbohydrate, does all of these effects without appreciably altering the acidity of the gastrointestinal contents. Its concomitant use with therapeutically effective amounts of anti-epigastralgic agents that reduce acidity, particularly, antacids was felt to adversely affect its strengths. This invention proves that this previous assumption of those skilled in the prior art, was erroneous.

The antacid substances, such as aluminum hydroxide, magnesium hydroxide and magaldrate gels neutralize the pH of the gastrointestinal contents. Some antacid materials, magnesium alginate particularly, treat non-ulcer mucosal irritations via the formation a of gelantinous foam or raft which floats on the stomach contents by entrapping gas. The floating foam creates a barrier between the irritating gastric contents and the irritated mucosal lining of the esophagus [U.S. Pat. No. 4,869,902; 4,140,760]. On the other hand, compounds known as H2-blockers like cimetidine, famotidine, omerapozole and ranitidine are examples of those substances that diminish acid production. But similar to antacid materials, H2 blockers are ineffective in binding bilious materials or significantly reducing the enzymatic activity of pepsin-like enzymes. The administration of such drugs as bethanechol (Urecholine ®) and meta-chlopramide (Reglan ®), which increase the tone of the lower esophageal sphincter and accelerate gastric emptying is also used to treat or prevent the symptoms of GI irritation by minimizing the time of physical contact of the esophageal mucosal with irritants in the gastric contents. However it too fails to deal directly with the major irritating substances, bile acids and digestive enzymes such as pepsin.

In the case where gastrointestinal irritation has become a fixed ulceration, treatment may involve pharmaceutical measures beyond those that neutralize acid, decrease its production or minimize its contact with mucosal lining. This alternate measure centers about the use of ulcer-adherent substances like sucralfate. Sucralfate is believed to heal by sticking to the bed of the ulcer. This act of sticking to the ulcer bed creates a visible physical barrier between the ulcer bed and the gastric contents [Ref 6]. Disruption of this physical barrier is commonly thought to diminish the ulcer-healing ability of sucralfate and sucralfate-like materials. However the ulcer-adherent qualities are only 1 out of the 5 probable mechanisms whereby sucralfate heals ulcers. Unanticipated by those skilled in the art, but as disclosed in this invention, four mechanisms persist uneffected in the presence of therapeutic amounts of antacid type of anti-epigastralgic agents.

Therefore the present invention introduces an unanticipated novel approach to treat those gastrointestinal mucosal conditions that result from the damaging contact of irritants such as gastric acid, bile acid and digestive enzymes. That approach is the concommitant administration, as a single composition, of poly[phosphoryl/sulfon]-ated carbohydrates with anti-epigastralgic agents, even anti-epigastralgic agents of the antacid variety.

Certain poly[phosphoryl/sulfon]-ated carbohydrates bind bile acids, mitigate the effects of gastric acid and inactivate certain digestive enzymes, in particular pepsin-like enzymes. Pharmaceutical compositions containing poly[phosphoryl/sulfon]-ated carbohydrate have never been used as anti-irritant component of any anti-eplgastralgic composition of matter to prevent or to treat mucosal irritation. A compositional embodiment of this invention involves the combination of poly[phosphoryl/sulfon]-ated carbohydrates with antacid materials so as to make a composition that not only effectively neutralizes gastric acid but also binds bile salts, reduces the enzymatic activity of pepsin and protects the mucosa from the attack by acid.

In this invention the functionalized carbohydrate are combined with anti-epigastralgic agents. A functionalized carbohydrate is any suitable poly[phosphoryl/sulfon]-ated carbohydrate, including sucralfate. Sucralfate and sucralfate-like materials had potential non-ulcer uses anticipated by Brooks et al [Ref 14]. Any suitable poly[phosphoryl/sulfon]-ated carbohydrate, including sucralfate and sucralfate-like materials, can bind bile salts and diminish the activity of pepsin-like enzymes. Heretofore such compounds had only been suggested for use either as an agent to cure fixed ulceration such as gastric ulcers, duodenal ulcers or as an agent to treat infection-mediated gastritis [U.S. Pat. Nos. 3,432,489; 4,935,406]. This invention suggests that sucralfate and other poly[phospho/sulfa]-nated carbohydrates can be used in compositions solely for the prevention and treatment of disorders of superficial gastrointestinal irritation not involving fixed ulcerations or mucosal irritations due to infection. Sucralfate-like materials have been the subject of many patent publications [U.S. Pat. Nos. 4,940,786; 4,935,406; 4,918,175; 4,912,093; 4,945,085; 4,945,084; 4,885,281; 4,851,209; 4,668,665]; in none of the claims reviewed is there mention of or implication of the single use of sucralfate-like material to ameliorate the symptoms and physical findings of superficial gastrointestinal irritation. Without exception, throughout the literature the mechanism of action attributed to sucralfate's ability to heal fix ulceration disease is related to its ability to physically bind to the bed of the ulcer. The fact that sucralfate-like substances and other poly[phosphoryl/sulfon]-ated carbohydrates, can indeed bind bile salts/acids, mitigate the effects of gastric acid and reduce the enzymatic activity of pepsins implicate their potential benefit in gastrointestinal protection against non-ulcer, non-infectious disorders such as reflux esophagitis, heartburn, acid indigestion, acid or bilious gastritis and duodenitis. This invention is a practical expression of this type of use and sucralfate is a prime example of the type of poly[phospho/sulfa]-nated carbohydrate compound that can be used in the compositions that embody this invention.

OPERATION OF THE INVENTION

The following lists the pharmacologic actions of an anti-acid/poly[phosphoryl/sulfon]-ated carbohydrate composition that demonstrate the operation of the present invention in its mechanism of alleviating gastrointestinal irritation. Mechanistically these compositions a) bind bile acids/salts; b) form a physically-coating barrier for the gastrointestinal mucosa from gastric contents; c) form a physiochemical barrier; d) inhibit the irritating enzymatic actions of gastric substances such as pepsin; e) create an increase resistance to the local effects of acid within the coated mucosa thereby mitigating the effects of gastric acid; f) provide the release the other active ingredients present within the compositions; and g) lower the pH. Sucralfate-containing compositions are the preferred embodiments of poly[phosphoryl/sulfon]-ated carbohydrate-containing pharmaceutical compositions. Such compositions counteract irritant effects and thereby facilitate the protection of or the treatment of superficial non-ulcer damage sustained within the gastrointestinal mucosa. Poly[phosphoryl/sulfon]-ated carbohydrate compositions of this invention operate the following actions:

a. Bind Bile Acid Material

Poly[phosphoryl/sulfon]-ated carbohydrate-containing compositions can treat or prevent the symptoms of gastrointestinal mucosal irritation because they have the ability to bind bile acid material effectively [Ref 21]. The strength of this binding is comparable to that of cholestyramine (Questran, Cholybar) which is used to lower cholesterol by binding bile acids in the intestinal lumen. The bile acid binding of poly[phosphoryl/sulfon]-ated carbohydrate-containing compositions is strong in acid pH falling off only slightly until pH 7. At pH 7, its binding 20–50% of that of cholestyramine [Ref 6]; the gastric contents rarely reach this pH naturally or even when treated with antacids. The clinical significance in binding such bile acid irritants has been illustrated in experimental models of bile-induced gastric ulcerations [Ref 4]. In this model, the animal undergoes surgical ligation of the bile duct with the subsequent development of bile-induced ulcerations. The incidence of bile induced ulcers in the stomach can be reduced by 72% in animals pre-treated with a poly[phosphoryl/sulfon]-ated carbohydrate-containing compositions compared to no reduction in the incidence of bile acid induced ulcers in animals pre-treated with misoprostol, famotidine or saline; that is, in the latter group, 100% developed bile-induced ulcerations despite pre-treatment with an H2 blocker or a prostaglandin agonist. This demonstrates that through the binding of bile acids poly[phosphoryl/sulfon]-ated carbohydrate-containing compositions, specifically sucralfate, can prevent the occurence of gastric irritation caused by the presence of bile in contact with the mucosa. Table 1 shows the percent of bile-induced ulcerations that developed in the presence of sucralfate.

TABLE 1

| Anti-ulcer Agent | Percent Developed Bile Ulcers | Percent Bile Ulcers Prevented | Number of Animals |
| --- | --- | --- | --- |
| Saline | 100% | 0% | n = 7 |
| Famotidine | 100% | 0% | n = 7 |
| Misoprostol | 100% | 0% | n = 7 |
| Sucralfate | 29% | 71% | n = 7 |

It is obvious that sucralfate, a poly[phosphoryl/sulfon]-ated carbohydrate, reduced the incidence of bile-induced ulcers through its ability to bind bile acids b. Form a Physical Barrier through Mucasal Coating Poly[phosphoryl/sulfon]-ated carbohydrate-containing compositions become a paste-like, viscous substance that physically adhere to the gastrointestinal mucosa and thereby provide a protective coat. In acid pH 3–4, poly[phosphoryl/sulfon]-ated carbohydrate-containing compositions, particularly sucralfate, has been observed by endoscopic examinations to become a "vicous gel" [Ref 3, Abstract line 10], a "paste like substance . . . [which] strongly adheres to the gastric and duodenal mucosa" [Ref 6, pg 648]. The paste-like substance is formed through the non-covalent polymerization of poly[phosphoryl/sulfon]-ated carbohydrate. This polymerization is visibly dramatic and it exemplifies how poly[phosphoryl/sulfon]-ated carbohydrate compounds react in an acid environment, a pH less than 3. The formation of this barrier relates to the dual solubility character of poly[phosphoryl/sulfon]-ated carbohydrate-containing compositions; specifically, sucralfate at pH less than 3 is partially dissociated, some of its aluminum hydroxide ions dissolving, but the sucrose octasulfate moiety of sucralfate at that pH is mostly insoluble [Ref 5]. Al pH greater than 4 the sucrose octasulfate moiety dissolves. The physical barrier of visible mucosal coating by the sucralfate gel does impede the action of certain irritants particularly pepsins [Ref 4,6].

c. Physiochemical Barrier

Sucralfate is basic aluminum hydroxide salt of sucrose octasulfate. See Merck Index 14th Edition, Merck & Co, Rahway N.J. (1985). The aluminum hydroxide molecules, 2 per sulfate group, partially dissociates at pH<3, while the dissolution of sucrose sulfate occurs at pH>4. The dissociated sucrose octasulfate selectively binds to mucin [Ref 5,17,19,20]. Protons from the gastric acid, bile salts and pepsin are thereby disallowed access to the cells of the mucosal lining.

Once dissociated however sucrose octasulfate is water soluble [Ref 16]. Experimental models have shown that a clear solution of sucrose sulfate component of sucralfate provide comparable mucosal resistance to proton influx [Ref 5,17], bile acid influx [Ref 17] and pepsin damage [Ref 17]. Morphologically the acid exposed rabbit mucosal lining can be preserved from evidence of injury [Ref 5,14], when a solution of sucrose octasulfate bathes the mucosa. The visible adherent substance formed from sucralfate polymerization need not be present to protect the mucosa from damage [Ref 5,17]. In fact clear solution of sucrose octasulfate diminishes gastric ulceration induced in rats by pyloric ligation [Ref 18]. However the sucralfate gel, by one study did appear to offer slightly more of a mucosal protective effect, in that zero out of six animals treated with sucralfate gel developed pepsin related injury while one out of six animals treated with the clear sucrose octasulfate solution developed an intramural hemmorhage from pepsin exposure [Ref 17]. The sucralfate gel physically binds pepsin [Ref 3] and by binding its mucoid substrate, a glycoprotein [19], disallows pepsin degradation of the mucus. Sucrose octasulfate while it does not physically bind pepsins, it does competively bind mucin, the substrate of pepsin. By binding to mucin, this sucralfate subcomponent, sucrose octasulfate, can significantly increase the viscosity of the mucus layer [Ref 20].

d. Inhibit the Activity of Irritative Digestive Enzymes

Poly[phosphoryl/sulfon]-ated carbohydrate-containing compositions inhibit the enzymatic activity of irritative digestive enzymes such as pepsin. Again, sucralfate-containing compositions are the preferred embodiments. At pH 1, pepsinogens are converted to their active forms called pepsins, which can irritate the GI mucosa. Above pH 2, sucralfate-containing compositions inhibit peptic activity by both adsorbing pepsin and by the release of buffering hydrogen ions [Ref 3]. As can be seen in Table 2 the normal activity of pepsin in gastric juice is reduced significantly by carbohydrate polysulfonates, while aluminum hydroxide, a conventional antacid material, which maximally reduces the overall pH, causes only a modest reduction in pepsin activity.

TABLE 2

| Poly (P/S)-ated CHO | Dose [mg/50 ml] | pH | Percent Pepsin Activity Present |
| --- | --- | --- | --- |
| Control | 0 | 1.3 | 100% |
| Al[OH]3 | 50 mg | 3.8 | 80% |
| Dextran Polysulfonate | 30 mg | 1.3 | 43% |
| Amylose Polysulfonate | 30 mg | 1.9 | 13% |
| Sucralfate | 30 mg | 2.8 | 43% |
| Sucralfate | 50 mg | 3.6 | 23% |
| Sucralfate | 100 mg | 3.7 | 21% | e. Causing the Mucosa to be More Resistant to Local Effects of Acid

Poly[phosphory/sulfon]-ated carbohydrate-containing compositions, of which sulcralfate-containing compositions are the preferred embodiments, mitigate the local effects of acid by making the epithelium resistant to acid. This effect is attributed to the carbohydrate polysulfonate molety of sucralfate and has been demonstrated experimentally [Ref 5]. The acid-neutralizing capacity of poly[phosphoryl/sulfon]-ated carbohydrates in solution is quite small; however they exert their neutralizing ability in a manner that differs from that of conventional antacid material. Conventional antacid material neutralizes whole soutions while poly[phosphoryl/sulfon]-ated carbohydrates act mainly at the gastric mucosal surface via their metal-hydroxyl moeity [Ref 5]. It provides focally fixed neutralization to acid thereby measurably increasing the epithelium's resistance to acid.

f. Unhindered Systemic Absorption of Other Components of the Composition

The absorption of co-administered aspirin is not affected by the presence of sucralfate [Ref 12]. The absorption of co-administered naproxen and ketoprofen is not affected by the presence of sucralfate [Ref 11]. Thus there is unhindered absorption of other active ingredients of the composition. Co-administration with acid reducing agents such as cimetidine, ranitidine, famotidine, nizatidine or omerprazole.

g. Lowering pH

The composition of this invention also lowers the pH by either acid neutralization, decrease secretion of new acid or both. Aniacid substances such as aluminum hydroxide, magnesium hydroxide, potassium or sodium bicarbonate, calcium carbonate, glycine, malgadrate, bismuth, citrate and magnesium carbonate. These substances will neutralize acid. Substances such as cimetidine, ranitidine, nizatidine and famotidine lower pH by decreasing secretion of newly formed acid. Either of each class or both simultaneously in combination with sucrose octasulfate and/or sucralfate embody this invention.

SUMMARY OF THE INVENTION

The invention relates to compositions of matter comprising functionalized carbohydrates with one or more epigastralgia relieving agent and the method of its use. Whether gastrointestinal irritation is inherent by virture of ongoing disease states or brought on by the intraluminal introduction of agents of potentially irritating effects, the compositions of this invention effectively minimize the ensuing mucosal irritation. Combining functionalized carbohydrates, specifically poly[phosphoryl/sulfon]-ated carbohydrates, of which sucralfate is a type, with other pharmaceuticals such as eplgastralgia-relieving agents impart to said pharmaceuticals the ability to bind bile acids/salts, mitigate the local effects of gastric acidity and diminish pepsinogenic activity in gastric secretions, said ability not being inherent to the pharmaceuticals prior to their combination with the poly[phosphoryl/sulfon]-ated carbonhydrate.

Epigastralgia-relieving agent include anti-gas and pH altering compounds such as: Simethicone, Aluminum Hydroxide, Magnesium Hydroxide, Potassium or Sodium Bicarbonate, Calcium Carbonate, Magnesium Carbonate, Cimetidine, Ranitidine, Nizatidine and Famotidine and gels or mixtures of any combination of the same. Magnesium Alginate and sucrose octasulfate are epigastralgia-relieving agents operating by their surface active effect on GI mucus [Ref. 5,17, U.S. Pat. No. 4,869,902; 4,140,760]. These agents combined with a poly[phosphoryl/sulfon]-ated carbonhydrate, such as sucralfate, in amounts sufficent to relieve epigastric and gastric discomfort, define an embodiment of the invention. The embodiments are group according to their compositional class. Simethecone alone or with another epigastralgia-relieving agent when combined with a poly[phosphoryl/sulfon]-ated carbohydrate, such as sucralfate, becomes an anti-gas anti-irritant composition. Aluminum hydroxide and magnesium hydroxide and calcium carbonate are anti-acid types of epigastralgia-relieving agent; these individually or together when combined with a poly[phosphoryl/sulfon]-ated carbohydrate, such as sucralfate, become antacid anti-irritant compositions. Alginate material and sucrose octasulfate, surface active epigastralgia-relieving agents individually or together when combined with a poly[phosphoryl/sulfon]-ated carbohydrate, such as sucralfate, become surface-active anti-irritant compositions.

BRIEF DESCRIPTION OF THE DRAWINGS

FIG. 1, PLOT 1 shows the rate of rise to therapeutic onset, i.e., neutralization to a pH of 3, as a function of time.

FIG. 1, PLOT 2 shows the rate of acid neutralizing effects as a function of time.

FIG. 2, BAR GRAPH 1 represents the percent of heartburn episodes relieved as a result of the adminstration of the claimed composition or the prior art composition at different times.

FIG. 2, BAR GRAPH 2 represents the percent of clinical improvement of the use of the claimed composition over the prior art at different times.

COMPOSITIONAL CONCENTRATIONS OF COMPONENTS

The composition of this invention is in either liquid or solid dose form specifically formulated such that the weight/weight ratio for functionalized carbohydrates like sucralfate and sucrose octasulfate and the epigastralgic-relieving agents listed would range respectively from 0.5:1.0 to 1.0:3.0. The epigastralgic-relieving agents are one or more of the following: simethicane, aluminum hydroxide, magnesium hydroxide, potassium or sodium bicarbonate, calcium carbonate, glycine citrate, bismuth, magnesium carbonate, malgadrate, cimetidine, ranitidine, nizatidine and famotidine. The combined compositional percent weight of functionalized carbohydrates and epigastralgic relieving agents is 10–30% per 5 millimeter of liquid volume or 40–85% per solid dose form. Examples of preferred embodiments are listed below in section entitled "Illustration of Invention".

METHOD OF USE NOVELTY OF THIS INVENTION OVER PRIOR ART

In marked contradistinction to prior art the inventor asserts that poly[phosphoryl/sulfon]-ated carbohydrates, particularly sucralfate, may be mixed with any therapeutic amounts of antacid materials to potentiate the utility of the antacid materials in treating or preventing both non-ulcer esophagogastrointestinal mucosal disorders as well as ulcerative ones.

ILLUSTRATION OF THE INVENTION

The following examples of this invention listed below are illustrative only; they are not at all intended to limit the scope of the invention, but rather to exemplify the practicality of this invention. These examples depict potential embodiments. The preferred embodiment of a poly[phosphoryl/sulfon]-ated carbohydrate-containing composition are those which contain sucralfate. It should be borne in mind, however, that other carbohydrate poly[phosphoryl/sulfon]-ates could be used as well. Also below are the results of clinical and laboratory experience of using Example #4 and #7 for treatment of gastrointestinal irritation.

LABORATORY AND CLINICAL ILLUSTRATION OF INVENTION

Correlation of In Vitro (Laboratory) Tests with In Vivo (Clinical) Tests of Antacid Drugs It is believed that antacids act by neutralization. Antacid raise the pH in the direction of pH7, but do not and need not completely neutralize acidity in the stomach. An antacid that raises the stomach contents from a pH of 1.5 to pH 3.5 has produced a 100-fold reduction in the concentration of acid. In other words, 99 percent of the initial acid has been neutralized.

In an attempt to standardize the methodology for the evaluation of antacids, Smyth et al (22) studied the rate and extent of acid consumption of antacids by in vitro and in vivo techniques. They found that the duration of elevation of intragastric pH above 3 as measured by a swallowed radiotelemetric capsule attached to a string, was in agreement with in-vitro estimates of total acid consumption of the antacid. There was good correlation between onset, extent, and duration of in vivo antacid activity and a modified in vitro Beekman antacid test procedure.

Methods of Laboratory Study

One of the objects of this invention is to create a good antacid effect. Two measurable properties of a good antacid effect is the 1) rapidity reaction with acid and 2) the ability to buffer the pH in a range between pH 3 to pH 6. The modified Beekman procedure (22. Smyth R. D., Herczeg T. et al: Correlation of In Vitro and In Vivo Methodology for Evaluation of Antacids. J Pharm Sci 65(7); 1045–47, 1976) was used to evaluate this invention in the specifically disclosed ratios as compared to the ratios suggested by the prior art (Harwood et al). The experimental setup is as follows: The antacid is added to 50 ml of 0.1 mol/liter hydrochloric acid and pH is recorded over time. After 6 minutes hydrochloric acid, 1 mol/liter, is added at a rate of 0.5 ml per min. The pH is recorded as a function of time. The results shown below are the average of 3 runs each of the modified Beekman procedure on Example #4 of this invention [250 mg sucralfate in 30 mEq per 5 ml volume] and of Harwood et al's 500 mg sucralfate in 10 mEq per 5 ml volume. Harwood et al preferred 5 mEq of antacid per 500 mg of sucralfate, but in his first claim mention the range of 0.5 to 10 mEq. So the largest antacid concentration of this range, 10 mEq, was selected knowing that it follows that weaker concentrations of antacid would perform less well. When examined, it made no difference in the neutralization capacity of the Harwood et al's invention, whether 250 mg of sucralfate or 500 mg of sucralfate was used as the embodiment. Again, out of interest of choosing the best representative embodiment of inventions of prior art, 500 mg of sucralfate was selected.

Results of Laboratory Study

FIG. 1 shows the plots of neutralization dynamics of this invention and of Harwood et al's as a function of time. Plot 1 of FIG. 1 shows the rate of rise of neutralization to the point of therapeutic onset, that is the rate of neutralization toward pH 3, while Plot 2 shows the entire expanse of acid-neutralizing effect as a function of time. As mentioned above, for therapeutic effect, the antacid effect must reach pH 3 and keep the pH above this value. The open boxes represent the invention of this application while the closed boxes represent the invention of Hardwood et al. It can be clearly seen that the rate of rise to pH 3 and the time spent above pH 3 for the invention of this application is superior to that of prior art.

The quantitation of this difference is shown in Table 3 below.

TABLE 3

IN VITRO STRENGTH OF NEUTRALIZATION:
Evidence of Superiority Over Prior Art

| MEASURED PARAMETER | THIS INVENTION (Example #4) | PRIOR ART [Control] | NUMBER OF ASSAYS | PERCENT [%] IMPROVEMENT OVER PRIOR ART |
|---|---|---|---|---|
| TIME TO REACH THERAPEUTIC pH of 3 | 10.0 ± 0.2 sec | 162.0 ± 5 sec | 3 | 15,000% |
| TIME SPENT ABOVE pH 3 in 45 min Assay | 44.0 ± 0.5 min | 22.0 ± 0.9 min | 3 | 100% |

Clinical Study

Nine human volunteers who suffer from sympton of gastrointestinal irritation were given both inventions of this application [Example #4 and #7] and the same inventions of prior art tested in laboratory study above. Both qualitative and quantitative assessments were made.

Methods of Qualitative Clinical Assessment

To nine human volunteers (whose profiles are listed below) Example #4 and #7 of this invention was given to treat the symptoms of their gastrointestinal mucosal irritation. Each participant was requested to rate the novel compostions in terms of speed of action, amount of relief as well as its taste, texture and smoothness.

| PROFILE OF PARTICIPANTS USING THIS INVENTION'S SUCRALFATE ANTACID EXAMPLE FORMULATIONS #4 & #7 | | | | | |
|---|---|---|---|---|---|
| Initials | Gender | Age | Symptom Frequency [Episodes/wk] | Agent Used Previously | Prior Ulcer |
| 1. AO | M | 61 | 2–3/wk | Mylanta | Yes |
| 2. JA | M | 64 | 2–4/wk | Rolaids/Cimetidine | Yes |
| 3. SB | M | 39 | 5–6/wk | Tums | Yes |
| 4. RT | F | 42 | 2–3/wk | Mylanta/Ranitidine | Yes |
| 5 EB | M | 65 | 4–5/wk | Mylanta | Yes |
| 6 RM | M | 39 | 1–2/wk | Bicarbonate Soda | No |
| 7. AT | M | 48 | 9–10/wk | Rolaids/Tums/Cimetidine | Yes |
| S. RM | M | 46 | 1–2/wk | Mylanta | Yes |
| 9. JM | F | 37 | 0–1/wk | Bicarbonate Soda | No |

Results of Qualitative Assessment

The volunteers were given four categories of answers: "Best Ever", "Better than Most", "Just OK", or "Could Be Better". Each of the volunteers tested stated that Formulation Example #4 and #7, a sucralfate antacid admixture and a sucralfate-H-2-blocker-antacid admixture, respectively were ether the "Best Ever" or "Better than Most" as regards its speed of action and the "Best Ever" or "Better than Most" as regards the amount of relief as well as its taste, texture and smoothness. Only one of the subjects [AT age 48 rated either of the embodiments of the invention as "Just OK" or "Could Be Better" in the category of taste.

Methods of Quantiative Clinical Assessment

As the laboratory (in vitro) tests have measureable qualities of the antacid effect so too the clinical assessment has the two measureable properties pertaining to the effectiveness of relief; they are 1) the rapidity of onset of relief and 2) the completeness of relief. The following study was conducted to assess these two characteristics.

Nine volunteers who experience some 36 different episodes of gastrointestinal irritation (heartburn, indigestion, post-prandial epigastric discomfort) were given compositions of this invention (5 ml of Example #4) and of Harwood el al (5 ml of 500 mg sucralfate in 10 mEq antacid per 5 ml) to relieve their episodes. As have been used in other studies a scoring system was established on a scale of 0.1 to 7.0, values assigned to descriptive outcomes such as "no relief, poor partial relief, moderate partial relief and complete relief" over a time period increments of 1 minute, 2 minutes, 5 minutes, 10 minutes and 20 minutes. There were 20 possible outcomes all of which were assigned some numerical value. The Table 4 below shows the assignment of these values to the various outcomes.

TABLE 4
VALUES OF POSSIBLE CLINICAL OUTCOMES

| TIME (MIN) | COMPLTE RELIEF | MODERTE PARTIAL | POORLY PARTIAL | NO RELIEF |
|---|---|---|---|---|
| 1 MIN | 7.0 | 2.8 | 1.8 | 0.8 |
| 2 MIN | 6.0 | 2.6 | 1.7 | 0.6 |
| 5 MIN | 5.0 | 2.4 | 1.6 | 0.4 |
| 10 MIN | 4.0 | 2.2 | 1.4 | 0.2 |
| 20 MIN | 3.6 | 2.0 | 1.2 | 0.1 |

Results of Quantitative Assessment

FIG. 2 shows the bar graphs of the clinical effectiveness of this invention (BAR GRAPH 1) and the percent of clinical improvement of this invention over prior art (BAR GRAPH 2). The clinical significance of the current invention over the prior art was striking. Table 5 list the raw data points regarding the time of onset of relief while. Table 6 shows the raw data points regarding the completeness of relief.

TABLE 5
TIME OF ONSET OF CLINICAL RELIEF

| FACTOR ASSESSED | THIS INVENTION | [CONTROL] PRIOR ART | TOTAL |
|---|---|---|---|
| WITHIN 5 MINUTES | 108.5 | 116.8 | 225.3 |
| REQUIRING MORE THAN 10 MINUTES | 27.0 | 86.4 | 113.4 |
| TOTAL | 135.5 | 203.20 | 338.7 |

TABLE 6
COMPLETENESS OF CLINICAL RELIEF

| FACTOR ASSESSED | THIS INVENTION | [CONTROL] PRIOR ART | TOTAL |
|---|---|---|---|
| COMPLETE RELIEF | 63.0 | 43.2 | 106.2 |
| PARTIAL RELIEF | 72.5 | 160.0 | 232.5 |
| TOTAL | 135.5 | 203.2 | 338.7 |

The data points in both Table 5 and Table 6 were subjected to statistical analysis using chi square method. The chi square value correlates with the probability of a null hypothesis that two groups of percentages are equal and equivalent. Applied to this study, the null hypothesis would be that the completeness of relief and the time of onset of relief experienced with the current invention is the same as that experienced with Harwood et al's invention. In general the larger the chi square value the smaller is the probability that the null hypothesis is true. The chi square values convert to p-values as follows:

| Chi Square Value | P-value |
|---|---|
| 0.46 | 0.5 |
| 2.71 | 0.1 |
| 3.84 | 0.05 |
| 6.64 | 0.01 |
| 10.83 | 0.001 |

As can be seen in Table 7 all chi square values were large for each category of assessment made. That is the time of onset of relief whether within 5 minutes or within the final 10 minutes were significantly different in favor of this invention by a large statistical margin. The completeness of relief was also significantly different in favor of this invention by a large statistical margin.

TABLE 7
QUANTITATIVE SUMMARY OF CLINICAL EXPERIENCE

| | THIS INVENTION (Example #4) | CONTROL (PRIOR ART) | PERCENT IMPROVEMENT OVER PRIOR ART | CHI SQUARE VALUE | STATISTICAL SIGNIFICANCE OVER PRIOR ART P-VALUE |
|---|---|---|---|---|---|
| SPEED OF ONSET | | | | | |
| Relief Within 5 minutes | 80.1% | 57.5% | 39.3% Improvement | 8.18 | $0.01 < p < 0.001$ |
| Requiring More than 10 minutes | 19.9% | 42.5% | 53.2% Reduction-Improvement | 8.26 | $0.01 < p < 0.001$ |
| COMPLETENESS OF RELIEF | | | | | |
| Partial Relief Only | 53.5% | 78.7% | 32.0% Reduction-Improvement | 10.65 | $0.01 < p < 0.001$ |
| Complete Relief | 46.5% | 21.3% | 118.3% Improvement | 10.66 | $0.01 < p < 0.001$ |

Example of a Liquid Suspension of Poly[phosphoryl/sulfon]-ated Carbohydrate with Surface Active Anti-Irriant Material The following examples illustrate for mulations wherein in the invention acts as a surface active anti-irritant material

Example 1
Poly[phosphoryl/sulfon]-ated Carbohydrates as Surface Active Anti-Irritant Materials using Sucrose Octasulfate

|  | mg/5 ml |
|---|---|
| Sucralfate or Amylose Polysulfate | 250–500 |
| Sucrose Octasulfate | 250–750 |
| Methyl Paraben USP | 5–10 |
| Propyl Paraben USP | 5–10 |
| Sodium Saccharin | 3.0–5.0 |
| Sorbitol USP | 200–350 |
| Flavor | q.s. |
| Water | 5000 |

In this example the sucrose octasulfate is used as a type of epigastralgia relleving agent, having surface-active anti-irritant activity.

Example 2
Poly[phosphoryl/sulfon]-ated Carbohydrates as Surface Active Anti-irritant Materials using Metal Alginate Substance

|  | mg/5 ml |
|---|---|
| Magnesium Alginate | 500–600 |
| Sucralfate [a poly[phosphoryl/sulfon]-ated carbohydrate] | 250–500 |
| ±Simethecone | 40–80 |
| Potassium Bicarbonate USP | 40–60 |
| Methyl Paraben USP | 5–10 |
| Propyl Paraben USP | 5–10 |
| Sodium Saccharin | 3.0–5.0 |
| Sorbitol USP | 200–350 |
| Flavor | q.s. |
| Water | 5000 |

In this example magnesium alginate is used as a type of epigastralgia relieving agent, having surface active anti-irritant activity.

Examples of a Liquid Suspension of Poly[phosphoryl/sulfon]-ated Carbohydrate-containing Antacid Material Poly[phosphoryl/sulfon]-ated carbohydrates in liquid form work better to alleviate symptomatic pain associated with gastrointestinal irritation. The symptoms of eplgastralgia, heartburn and nausea are less in individuals given a suspension of a poly[phosphoryl/-sulfon]-ated carbohydrate-containing material, such as liquid sucralfate, than in individuals given equivalent amounts of sucralfate in a solid dose form. Table 8 demonstrates this fact [Ref. 10.

TABLE 8

| Preparation Used | Percent Persons Without Symptoms of GI Irritation | |
|---|---|---|
|  | At 42 Days of Treatment | At 56 Days of Treatment |
| Sucralfate Tablets | 68% | 68% |
| Cimetidine | 72% | 80% |
| Sucralfate Liquid | 98% | 98% |

EXAMPLE 3
Formulations of Liquid Aluminum Hydroxide/Magnesium Hydroxide/Sucralfate

|  | mg/5 ml |
|---|---|
| Aluminum Hydroxide | 400–500 |
| Magnesium Hodroxide | 400–500 |
| Sucralfate [a poly[phosphoryl/sulfon]-ated carbohydrate] | 250–500 |
| ±Simethecone | 40–80 |
| Potassium Bicarbonate USP | 40–60 |
| Methyl Paraben USP | 5–10 |
| Propyl Paraben USP | 5–10 |
| Sodium Saccharin | 3.0–5.0 |
| Sorbitol USP | 200–350 |
| Flavor | q.s. |
| Water | 5000 |

EXAMPLE 4
Formulations of Liquid Magaldrate/Sucralfate

|  | mg/5 ml |
|---|---|
| Magaldrate | 500–1100 |
| Sucralfate [a poly[phosphoryl/sulfon]-ated carbohydrate] | 250–500 |
| ±Simethecone | 40–80 |
| Methyl Paraben USP | 5–10 |
| Propyl Paraben USP | 5–10 |
| Sodium Saccharin | 3.0–5.0 |
| Sorbitol USP | 200–350 |
| Flavor | q.s. |
| Water | 5000 |

EXAMPLE 5
Formulations of Liquid Magnesium Alginate/Aluminum Hydroxide/Sucralfate

|  | mg/5 ml |
|---|---|
| Magnesium Alginate | 500–600 |
| Aluminum Hydroxide-Magnesium Carbonate Gel | 150–300 |
| Sucralfate [a poly[phosphoryl/sulfon]-ated carbohydrate] | 250–500 |
| ±Simethecone | 40–80 |
| Potassium Bicarbonate USP | 40–60 |
| Methyl Paraben USP | 5–10 |
| Propyl Paraben USP | 5–10 |
| Sodium Saccharin | 3.0–5.0 |
| Sorbitol USP | 200–350 |
| Flavor | q.s. |
| Water | 5000 |

EXAMPLE 6
Formulations of Liquid Calcium Carbonate/Magnesium Carbonate/Sucralfate

|  | mg/5 ml |
|---|---|
| Calcium Carbonate | 400–500 |
| Sucralfate [a poly[phosphoryl/sulfon]-ated carbohydrate] | 250–500 |
| ±Simethecone | 40–80 |
| Methyl Paraben USP | 5–10 |
| Propyl Paraben USP | 5–10 |
| Sodium Saccharin | 3.0–5.0 |
| Sorbitol USP | 200–350 |
| Flavor | q.s. |
| Water | 5000 |

EXAMPLE 7
Formulations of Liquid Acid Reduction Anti-Epigastrlgics/Sucralfate Type Compound

|  | mg/5 ml |
|---|---|
| Cimetidine or Ranitidine or Nizatidine or Famotidine or Omerprazole | 20–300 |
| Calcium Carbonate | 400–500 |
| Sucralfate [a poly[phosphoryl/sulfon]-ated carbohydrate] or Sucrose Octasulfate | 100–500 |
| ±Simethecone | 40–80 |
| Methyl Paraben USP | 5–10 |
| Propyl Paraben USP | 5–10 |
| Sodium Saccharin | 3.0–5.0 |
| Sorbitol USP | 200–350 |
| Flavor | q.s. |
| Water | 5000 |

Examples of Tablets of Poly[phosphoryl/sulfon]-ated Carbohydrate-containing Antacid Material Poly[phosphoryl/sulfon]-ated carbohydrates may be tableted with antacids by wet granulation or direct co-compression into a chewable or swallowable solid dose form.

EXAMPLE 8
Tablets of Aluminum Hydroxide/Magnesium Hydroxide/Sucralfate

| | mg/tablet |
|---|---|
| Aluminum Hydroxide | 400–500 |
| Magnesium Hodroxide | 400–500 |
| Sucralfate [a poly[phosphoryl/sulfon]-ated carbohydrate] | 250–500 |
| ±Simethecone | 40–80 |
| Polyethylene Glycol | 40–100 |
| Sucrose/Lactose | 60–80 |
| Corn Starch | 40–60 |
| Carboxymethyl Cellulose | 10–20 |
| Magnesium Stearate | 1.0–1.5 |
| Flavor | q.s. |

EXAMPLE 9
Tablets of Magadrate/Sucralfate

| | mg/tablet |
|---|---|
| Magaldrate | 500–1000 |
| Sucralfate [a poly[phosphoryl/sulfon]-ated carbohydrate] | 250–500 |
| ±Simethecone | 40–80 |
| Polyethylene Glycol | 40–100 |
| Sucrose/Lactose | 60–80 |
| Corn Starch | 40–60 |
| Carboxymethyl Cellulose | 10–20 |
| Magnesium Stearate | 1.0–1.5 |
| Flavor | q.s. |

EXAMPLE 10
Tablets of Magnesium Alginate/Sucralfate

| | mg/tablet |
|---|---|
| Magnesium Alginate | 500–600 |
| Aluminum Hydroxide-Magnesium Carbonate Gel | 150–300 |
| Sucralfate [a poly[phosphoryl/sulfon]-ated carbohydrate] | 250–500 |
| ±Simethecone | 40–80 |
| Polyethylene Glycol | 40–100 |
| Sucrose/Lactose | 60–80 |
| Corn Starch | 40–60 |
| Carboxymethyl Cellulose | 10–20 |
| Magnesium Stearate | 1.0–1.5 |
| Flavor | q.s. |

EXAMPLE 11
Tablets of Calcium Carbonate/Magnesium Carbonate/Sucralfate

| | mg/tablet |
|---|---|
| Calcium Carbonate | 400–500 |
| Sucralfate [a poly[phosphoryl/sulfon]-ated carbohydrate] | 100–500 |
| ±Simethecone | 40–80 |
| Polyethylene Glycol | 40–100 |
| Sucrose/Lactose | 60–80 |
| Corn Starch | 40–60 |
| Carboxymethyl Cellulose | 10–20 |
| Magnesium Stearate | 1.0–1.5 |
| Flavor | q.s. |

EXAMPLE 12
Tablets of Acid Reduction Anti-Epigastrlgics/Sucralfate Type Compound

| | mg/tablet |
|---|---|
| Cimetidine or Ranitidine or Nizatidine or Famotidine of Omerprazole | 20–300 |
| Calcium Carbonate | 400–500 |
| Sucralfate [a poly[phosphoryl/sulfon]-ated carbohydrate] or Sucrose Octasulfate | 100–500 |
| ±Simethecone | 40–80 |
| Sodium Saccharin | 3.0–5.0 |
| Corn Starch | 40–60 |
| Carboxymethyl Cellulose | 10–20 |
| Magnesium Stearate | 1.0–1.5 |
| Flavor | q.s. |

CONCLUSION AND SCOPE OF INVENTION

The invention is not limited to what is described in the above examples. It will be obvious to persons skilled in the art that alterations may be made without departing from the scope of this invention, which scope is defined by the following claims.

REFERENCES

1. Tarnawski, A. et al: The mechanism of protective, therapeutic and prophylactic actions of sucralfate. Scand J. Gastroenterol 22:7–13, 1987.
2. Koelz H. R.: Protective drugs in the treatment of gastroduodenal ulcer disease. Scand J. Gastroenterol 21[suppl125]: 156–163, 1986.
3. Samloff, I. M.; O'Dell, C: Inhibition of peptic activity by sucralfate. Am J Med 79: [suppl 2c]: 15–18, 1985.
4. Stapleton G. N. et al: Sucralfate in the prevention of porcine experimental peptic ulceraton. Am J Med 86[suppl 6a]:21–22, 1989.
5. Orlando R. C. et al: Mucosal protection by sucralfate and its components in acid-exposed rabbit esophagus. Gastroenterol 93: 352–61, 1987.
6. Guth, P. H.: Mucosal coating agents and other nonantisecretory agents/Are they cytoprotective? Dig Dis Sci 32: 647–654, 1987.
7. Borrero, E. et al: Comparison of antacid and sucralfate in the prevention of gastrointestinal bleeding in patients who are critically ill. Am J Med 79[suppl 2c]: 62–64, 1985.
8. Physician's Desk Reference: Carafate Informational Insert.
9. Tarnawski A. et al: Effect of sucralfate on normal human gastric mucosa. Endoscopic, histologic, and ultrastructural assessment [abstr] Gastrointest Endosc 30:155, 1984.
10. Arguelles-Martin F.; Gonzalez-Fernandez F.; Gentiles M.: Sucralfate versus cimetidine in the treatment of reflux esophagitis in children. Am J Med 86[suppl 6a]:73–76, 1989.
11. Caille G. et al: Effects of food and sucralfate on the pharmacokinetics of naproxen and ketoprofen in humans. Am J Med 86(suppl 6a):38–44, 1989.
12. Konturek S. J. et al: Double blind controlled study on the effect of sucralfate on gastric progstaglandin formation and microbleeding in normal and aspirin treated man. Gut 27:1450–1456, 1986.
13. Hollander D. et al: Protective effect of sucralfate against alcohol-induced gastric mucosal injury in the rat. Macroscopic, histologic, ultrastructural and functional time sequence analysis. Gastroenterol 88:366–74, 1985.
14. Brooks W. S. et al: Sucralfate: Nonulcer Uses. Am J Gastroent 80(3): 206–209, 1985.
15. McCullough R. W.: Sucrose Octasulfate Aluminum Salt and Dissacharide Polysulfate metal salts as an pharmaceutic excipient to protect the GI tract from local irritants. PTO Disclosure Doc No. 267,317 Nov. 14, 1990.
16. Nagashima R. et al: Sucralfate, a basic aluminum salt of sucrose I. Behavior in gastroduodenal pH. Arzrsch/Drug Res 29(11):1668–76, 1979].

17. Schweitzer E. J. et al: Sucralfate prevents experimental peptic esophagitis in rabbits. Gastroenterol 88:611-19, 1985.
18. Nagashima R. Development and characteristics of sucralfate. J Clin Gastroenterol 3[suppl 2]:103-10, 1981.
19. Slomiany B. et al: In vivo inhibition of peptic degradation of porcine gastric mucus glycoprote in by sucralfate. Scand J. Gastroenterol 20: 857-60, 1985.
20. Murty V. L. N. et al: Effect of sucralfate on the viscosity and retardation of hydrogen ion diffusion by gastric mucus. Gastroenterol 88: 1985.
21. Tanghoj, H. et al: Effects of sucralfate and cholestyramine on bile acid absorption. Gastroenterol 88(5), May 1985.
22. Smyth R. D., Herczeg T. et al: Correlation of In Vitro and In Vivo Methodology for Evaluation of Antacids. J Pharm Sci 65(7): 1045-47, 1976.
23. Evreux M.: Sucralfate, Alginate & Antacid in treatment of Gastroesophageal reflux. Amer J Med 83(Suppl 3B):48, 1987.

I claim:

1. A method of relieving symptoms of gastrointestional mucosal irritation in mammals comprising administering to said mammals a composition comprising sucralfate in combination with one or more anti-acid epigastralgic relieving agents in a weight to weight ratio of between 0.5:1.0 to 1:3 of sucralfate to antiacid epigastralgic relieving agent, said composition being in either liquid or solid dose form having a combined composition weight percentage of 10-30% per 5 milliliter volume of liquid or 40-85% per solid unit dose form.

2. A method of claim 1 wherein the epigastralgic relieving agent is bismuth.

3. A method of claim 1 wherein the epigastralgic relieving agents are simethicone and metal salt of alginate.

4. A method of claim 1 wherein the epigastralgic relieving agent is selected from the group consisting of cimetidine, ranitidine, nizatidine, famotidine and omerprazole.

5. A method of claim 1 wherein the epigastralgic relieving agent is simethicone.

6. A method of claim 1 wherein the epigastralgic relieving agent comprises one or more of the agents selected from the group consisting of: aluminum hydroxide, magnesium hydroxide, calcium carbonate, magnesium carbomate, malgadrate, glycine, bismuth and citrate in amounts sufficient 10 give 10 or more milliequivalents of acid neutralizing capacity per administered dose.

7. A method of claim 1 wherein the epigastralgic relieving agent is a metal salt of alginate.

8. A gastrointestional anti-irritant composition comprising sucralfate and one or more antiacid epigastralgic relieving agents selected from the group consisting of aluminum hydroxide, magnesium hydroxide, potassium bicarbonate, sodium bicarbonate, calcium carbonate, glycine, malgadrate, citrate, bismuth, magnesium carbonate cimetidine, ranitidine, nizatidine, and famotidine, in a weight to weight ratio of between 0.5:1.0 to 1:3 of sucralfate to the antiacid epigastralgic relieving agent, said composition being in either liquid or solid form having a combined composition weight percentage of 10-30% per 5 milliliter volume of liquid or 40-85% per solid unit form.

9. A gastrointestional anti-irritant composition of claim 8 wherein one of the epigastralgic relieving agents is simethicone.

10. A gastrointestional anti-irritant composition of claim 8 wherein one of the epigastralgic relieving agents is a metal salt of alginate.

11. A gastrointestional anti-irritant composition of claim 8 wherein one of the epigastralgic relieving agents is omerprazole.

12. A gastrointestional anti-irritant composition of claim 8 wherein the epigastralgic relieving agent is one or more antacid materials in amount of 10 milliequivalents or more of acid neutralizing capacity per administered dose.

* * * * *